(12) United States Patent
Oguri et al.

(10) Patent No.: US 11,382,597 B2
(45) Date of Patent: Jul. 12, 2022

(54) ULTRASONIC APPARATUS AND METHOD FOR APPLYING GAIN REDUCTION

(71) Applicant: General Electric Company, Schenectady, NY (US)

(72) Inventors: Takuma Oguri, Tokyo (JP); Yanyang Ju, Tokyo (JP)

(73) Assignee: General Electric Company, Schenectady, NY (US)

( * ) Notice: Subject to any disclaimer, the term of this patent is extended or adjusted under 35 U.S.C. 154(b) by 197 days.

(21) Appl. No.: 16/717,150

(22) Filed: Dec. 17, 2019

(65) Prior Publication Data

US 2020/0196978 A1 Jun. 25, 2020

(30) Foreign Application Priority Data

Dec. 21, 2018 (JP) .............................. JP2018-239027

(51) Int. Cl.
| | |
|---|---|
| *A61B 8/06* | (2006.01) |
| *A61B 8/14* | (2006.01) |
| *A61B 8/00* | (2006.01) |
| *G01S 7/52* | (2006.01) |
| *A61B 8/08* | (2006.01) |

(52) U.S. Cl.
CPC .............. *A61B 8/06* (2013.01); *A61B 8/0883* (2013.01); *A61B 8/0891* (2013.01); *A61B 8/14* (2013.01); *A61B 8/488* (2013.01); *A61B 8/5246* (2013.01); *A61B 8/54* (2013.01); *G01S 7/52033* (2013.01)

(58) Field of Classification Search
CPC . G01S 7/52033; G01S 15/8979; A61B 8/488; A61B 8/5246; A61B 8/0883; A61B 8/0891; A61B 8/54
See application file for complete search history.

(56) References Cited

U.S. PATENT DOCUMENTS

| | | | | | |
|---|---|---|---|---|---|
| 4,662,380 | A | * | 5/1987 | Riley | ................... G01S 7/52033 600/443 |
| 5,961,460 | A | * | 10/1999 | Guracar | ................... A61B 8/14 600/440 |
| 9,146,314 | B2 | * | 9/2015 | Sato | ......................... A61B 8/13 |
| 2003/0236460 | A1 | | 12/2003 | Ma | |
| 2009/0306503 | A1 | * | 12/2009 | Srinivasan | .............. A61B 8/461 600/441 |

(Continued)

*Primary Examiner* — Oommen Jacob
*Assistant Examiner* — Nyrobi Celestine

(57) ABSTRACT

[Problem] To provide an ultrasonic apparatus with which a decision can be made with better precision as to whether or not to apply gain reduction processing to a gain for echo signals.
[Means for Solution] An ultrasonic diagnostic apparatus comprises a control circuit executing: a creating function of creating, based on echo signals from first ultrasound transmitted to a subject to be examined, data for a B-mode image having brightness depending upon intensity of the echo signals; a motion detecting function of detecting a velocity value, etc. as information on motion in the subject based on echo signals from second ultrasound transmitted to said subject; and a deciding function of, in a case that the intensity of the echo signals from said first ultrasound is smaller than a first threshold th1 and said velocity value is equal to or greater than a second threshold th2, deciding that a gain for the echo signals from said first ultrasound is a target of gain reduction processing.

12 Claims, 8 Drawing Sheets

(56) References Cited

U.S. PATENT DOCUMENTS

| | | | |
|---|---|---|---|
| 2010/0069757 A1* | 3/2010 | Yoshikawa | A61B 5/02007 600/454 |
| 2013/0004047 A1* | 1/2013 | Shiki | G01S 7/52033 382/131 |
| 2013/0303907 A1* | 11/2013 | Corl | A61B 8/445 600/441 |
| 2015/0025380 A1* | 1/2015 | Azegami | A61B 8/5223 600/438 |
| 2017/0112473 A1* | 4/2017 | Samset | A61B 8/06 |
| 2017/0150948 A1* | 6/2017 | Kanayama | G01S 7/52071 |
| 2019/0261952 A1* | 8/2019 | Freiburger | A61B 8/488 |

* cited by examiner

ULTRASONIC APPARATUS AND METHOD FOR APPLYING GAIN REDUCTION

CROSS-REFERENCE TO RELATED APPLICATIONS

This specification is based upon and claims the benefit of priority from Japanese patent application number JP 2018-239027 filed on Dec. 21, 2018, the entire contents of which are incorporated herein by reference.

FIELD OF THE INVENTION

The present invention relates to an ultrasonic apparatus for performing gain adjustment, and a method for controlling an ultrasonic apparatus.

BACKGROUND

Among ultrasonic apparatuses, there is one having an automatic gain adjusting function, such as an automatic TGC (Time Gain Control) function. In the automatic gain adjusting function is sometimes encountered a case in which a decision is made before gain adjustment processing based on image brightness (intensity of echo signals) as to whether a non-noise portion, such as a tissue portion, is found or a noise portion is found, and gain adjustment is performed using gains different between the portion decided to be noise and the portion decided not to be noise (decided to be non-noise). For example, a portion having brightness (intensity of echo signals) equal to or lower than a threshold is decided to be a noise portion, and a portion having brightness (intensity of echo signals) higher than the threshold is decided to be a non-noise portion. For echo signals decided to be in a noise portion, noise can be suppressed by lowering the gain (see Patent Document 1, for example). For echo signals decided to be in a non-noise portion, the gain is raised to enhance them.

PRIOR-ART REFERENCE

Patent Document

[Patent Document 1] Japanese Patent No. 4405017

SUMMARY OF THE INVENTION

Problem to be Solved by the Invention

The inventors of the present application have studied improvements on the aforementioned noise decision technique. Specifically, noise sometimes exhibits a brightness value (intensity of echo signals) higher than a threshold. For example, when multiple reflection of ultrasound caused by a blood vessel wall occurs in a blood vessel, noise sometimes exhibits brightness higher than a threshold. Moreover, noise exhibiting brightness higher than a threshold sometimes occurs in a heart as well. In such cases, the aforementioned technique cannot lower a gain for the noise exhibiting signal intensity higher than a threshold, and in turn, cannot suppress noise. Accordingly, the inventors of the present application have studied a decision technique having better precision about whether to apply gain reduction processing to a gain for echo signals, and finally made the invention of the present application.

Means for Solving the Problem

The invention, in one aspect, for solving the aforementioned problem is an ultrasonic apparatus comprising a control circuit executing: a creating function of creating, based on echo signals from first ultrasound transmitted to a subject to be examined, data for an ultrasonic image having display information depending upon intensity of said echo signals; a motion detecting function of detecting information on motion in said subject based on echo signals from second ultrasound transmitted to said subject; and a deciding function of deciding whether or not a gain for the echo signals from said first ultrasound is a target of gain reduction processing based on the intensity of the echo signals from said first ultrasound and on said information on motion.

Effect of the Invention

According to the invention in the aspect, a decision can be made with better precision by the deciding function deciding whether or not a gain for echo signals from the first ultrasound is a target of gain reduction processing based on intensity of echo signals from the first ultrasound, and in addition, on the information on motion.

EMBODIMENTS FOR CARRYING OUT THE INVENTION

Now embodiments of the present invention will be described. The following description will be addressed to an ultrasonic diagnostic apparatus for displaying an ultrasonic image of a subject to be examined for the purpose of diagnosis, etc., as an example of the ultrasonic apparatus in accordance with the present invention.

Figure 1:
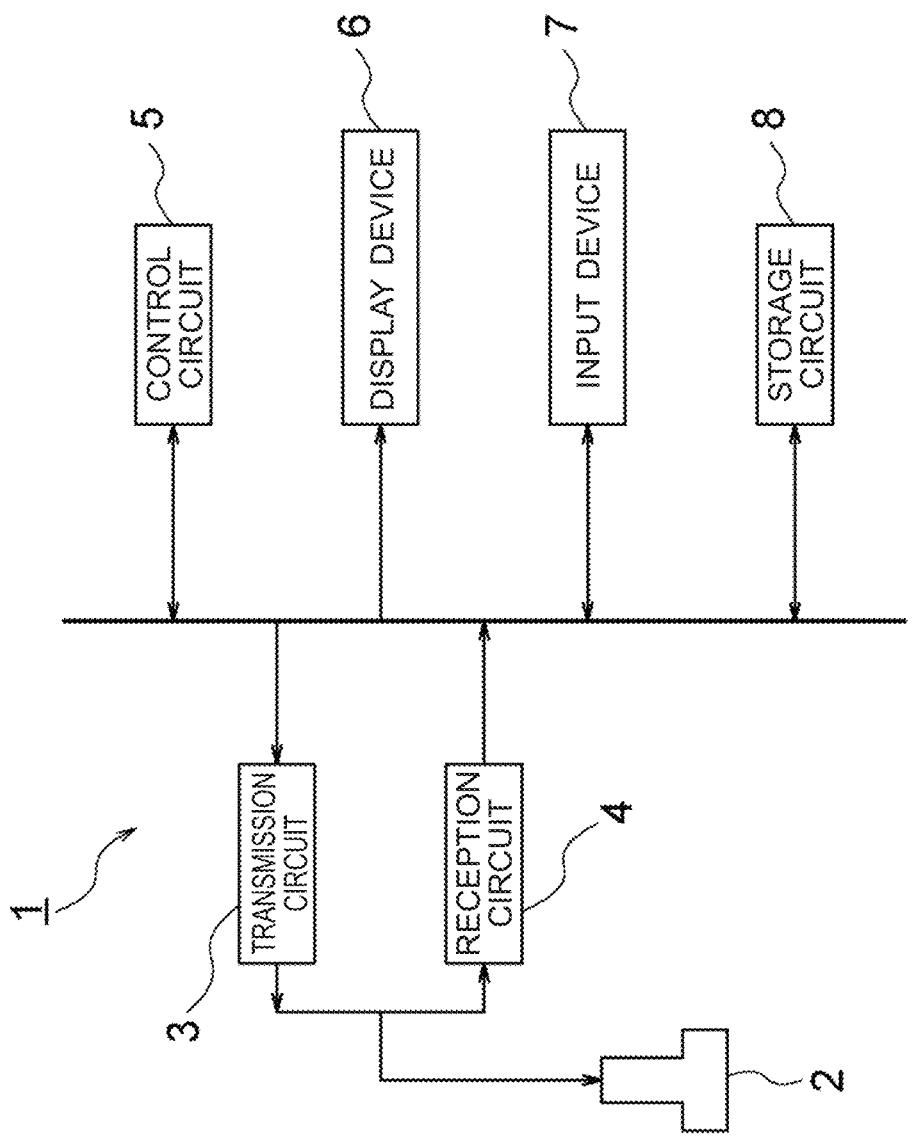
FIG. 1 A block diagram showing an exemplary ultrasonic diagnostic apparatus in an embodiment.

An ultrasonic diagnostic apparatus 1 shown in FIG. 1 comprises an ultrasonic probe 2, a transmission circuit 3, a reception circuit 4, a control circuit 5, a display device 6, an input device 7, and a storage circuit 8. The ultrasonic diagnostic apparatus 1 has a configuration as a computer.

The ultrasonic probe 2 has ultrasonic transducers (not shown), in which ultrasound is transmitted to biological tissue in a subject to be examined, and echo signals therefrom are received.

The transmission circuit 3 controls ultrasound transmission by the ultrasonic probe 2. Specifically, the transmission circuit 3 drives the ultrasonic probe 2 based on control signals from the control circuit 5 to transmit ultrasound having predetermined transmission parameters.

The reception circuit 4 applies signal processing, such as phased-addition processing, to the echo signals from ultrasound transmitted to the subject from the ultrasonic probe 2, reflected in the inside of the subject, and received at the ultrasonic probe 2. The reception circuit 4 performs the signal processing based on a control signal from the control circuit 5.

The transmission circuit 3 and reception circuit 4 may be constructed from hardware. However, instead of the configuration comprising such transmission circuit 3 and reception circuit 4 as hardware, the ultrasonic diagnostic apparatus 1 may be configured to implement functions of the transmission circuit 3 and reception circuit 4 by software. That is, the apparatus 1 may be configured such that the control circuit 5 loads programs stored in the storage circuit 8 and executes the aforementioned functions of the transmission circuit 3 and reception circuit 4.

The control circuit 5 controls several sections in the ultrasonic diagnostic apparatus to perform several kinds of signal processing, image processing, and the like. The control circuit 5 may include one or more processors, for example. Optionally, the control circuit 5 may include a central processor unit (CPU), one or more microprocessors, graphic processor units (GPU), or any other electronic components capable of processing input data following specific logic instructions. The control circuit 5 is capable of loading a program stored in the storage circuit 8 to execute its instructions. The storage circuit 8 here is a tangible non-transitory computer-readable medium, which will be discussed later.

Figure 2:
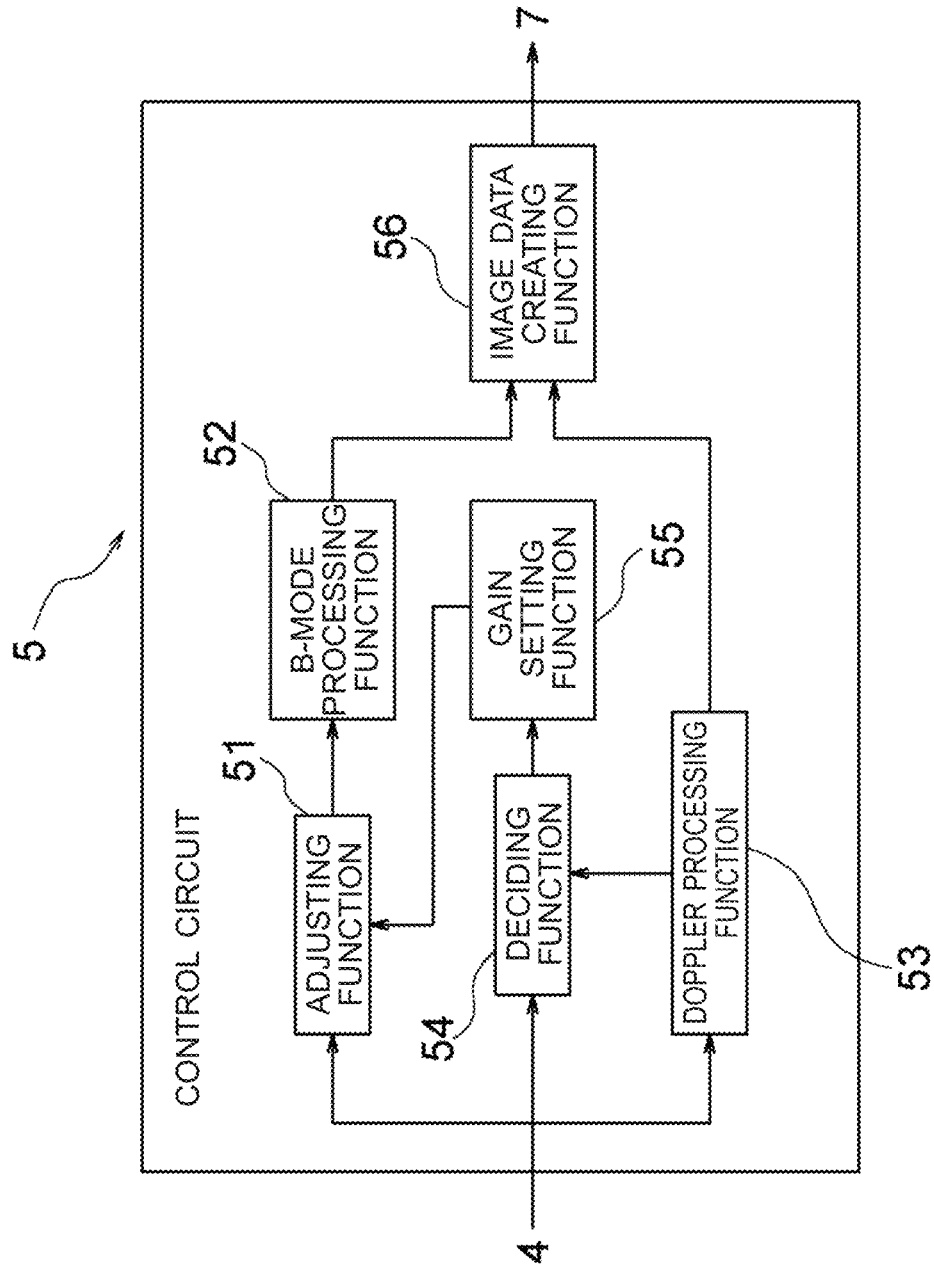
FIG. 2 An exemplary block diagram of functions of a control circuit in the ultrasonic diagnostic apparatus in the embodiment.

FIG. 2 is an exemplary functional block diagram of the control circuit 5 in the present embodiment. The control circuit 5 executes an adjusting function 51, a B-mode processing function 52, a Doppler processing function 53, a deciding function 54, a gain setting function 55, and an image data creating function 56. The control circuit 5 loads programs from the storage circuit 8, and executes these functions. While the control circuit 5 is shown in FIG. 2 as a functional block diagram, it may be configured as a complex of circuits and/or software modules. The control circuit 5 may also be implemented using any combination of a dedicated hardware board, a DSP (Digital Signal Processor), one or more processors, FPGAs (Field Programmable Gate Arrays), ASICs (Application Specific Integrated Circuits), and/or a tangible non-transitory computer-readable medium configured to issue instructions to the one or more processors. The control circuit 5 is an exemplary embodiment of the control circuit in the present invention.

The adjusting function 51 is a function of adjusting a data value of echo data output from the reception circuit 4 using a gain set by the gain setting function 55. The echo data here is first echo data obtained by B-mode-imaging ultrasound transmission/reception. The adjusting function by the adjusting function 51 includes attenuation processing for attenuating echo data, and enhancement processing for enhancing echo data. By the attenuation processing, it is possible to reduce noise in a B-mode image. The adjusting function 51 is an exemplary embodiment of the adjusting function in the present invention. The first echo data obtained by B-mode-imaging ultrasound transmission/reception is an exemplary embodiment of the echo signals from the first ultrasound in the present invention.

The B-mode processing function 52 is a function of applying B-mode processing including logarithmic compression processing, envelope detection processing, etc. to the echo data adjusted by the adjusting function 51 to create B-mode data.

The Doppler processing function 53 is a function of applying Doppler processing to the echo data output from the reception circuit 4 to create Doppler data. The echo data here is second echo data obtained by Doppler-processing ultrasound transmission/reception. By the creation of Doppler data by the Doppler processing function 53, information on motion in the subject can be detected. The Doppler processing is color Doppler processing, for example. The Doppler processing function 53 is an exemplary embodiment of the motion detecting function in the present invention. The second echo data obtained by the Doppler-processing ultrasound transmission/reception is an exemplary embodiment of the echo signals from the second ultrasound in the present invention.

The deciding function 54 is a function of deciding whether or not the echo data that is a target of adjustment by the adjusting function 51 is a target of gain reduction processing based on the data value of the echo data and on the Doppler data output from the reception circuit 4. The echo data used by the deciding function 54 is the first echo data obtained by the B-mode-imaging ultrasound transmission/reception. The decision technique will be discussed in detail later. The deciding function 54 is an exemplary embodiment of the deciding function in the present invention. The data value of the first echo data is an exemplary embodiment of the intensity of echo signals from the first ultrasound in the present invention. The Doppler data is an exemplary embodiment of the information on motion in the present invention.

The gain setting function 55 is a function of setting a gain used in adjustment on the echo data by the adjusting function 51 following the decision by the deciding function 54. The setting of a gain by the gain setting function 55 is defined as gain adjustment processing. Of the gain adjustment processing, setting of a gain less than one is defined as gain reduction processing. The gain setting function 55 is an exemplary embodiment of the gain setting function in the present invention.

The image data creating function 52 is a function of scan-converting the B-mode data by a scan converter to create B-mode image data. The image data creating function may also create color Doppler image data based on the Doppler data.

The B-mode processing function 52 and image data creating function 56 constitute an exemplary embodiment of the creating function in the present invention. The B-mode data and B-mode image data constitute exemplary embodiments of the data for an ultrasonic image in the present invention.

Returning to FIG. 1, the display device 6 is an LCD (Liquid Crystal Display), an organic EL (Electro-Luminescence) display, or the like. On the display device 6 is displayed, for example, a B-mode image produced based on the B-mode image data and having brightness information that is display information depending upon the intensity of echo signals.

The input device 7 is a device for accepting an operation by an operator, such as an input of a command, an input of information, and the like. The input device 7 is configured to comprise buttons, a keyboard, and the like for accepting the operator's inputs of a command and/or information, and to further comprise a pointing device, such as a trackball, and/or the like. Note that the buttons include soft keys displayed on the display device 6, as well as hard keys. The input device 7 may also comprise a touch panel. In this case, the buttons include soft keys displayed on the touch panel.

The storage circuit 8 may be a tangible non-transitory or transitory computer-readable medium, including flash memory, a hard disk, RAM, ROM, and/or EEPROM. The storage circuit 8 may be used to store B-mode data, B-mode image data, Doppler data, color Doppler image data, and other text and figures to be displayed on the display device 6, as well as other data. The storage circuit 8 may also be used to store the echo data output from the reception circuit 4. The echo data output from the reception circuit 4 includes the first echo data obtained by the B-mode-imaging ultrasound transmission/reception, and the second echo data obtained by the Doppler-processing ultrasound transmission/reception.

Additionally, the storage circuit 8 may be used to store acquired B-mode data, B-mode image data, Doppler data, and color Doppler image data that are not scheduled for instant display.

The storage circuit 8 may also be used to store firmware or software corresponding, for example, to graphical user interface, one or more default image display settings, and/or programmed instructions (for the control circuit 5, for example).

Next, an operation of the ultrasonic diagnostic apparatus 1 in the present embodiment will be described. The ultrasonic probe 2 performs B-mode-imaging ultrasound transmission/reception to/from a subject to be examined. First echo data is thus acquired. In the present embodiment, the ultrasound transmission/reception to/from a body part in the subject including a blood vessel is performed, and the first echo data is acquired. The ultrasonic probe 2 also performs Doppler-processing ultrasound transmission/reception to/from the same cross section in the subject as that to/from which the B-mode-imaging ultrasound transmission/reception is performed. Second echo data is thus acquired. The Doppler processing function 53 applies color Doppler processing to the second echo data to obtain color Doppler data.

The deciding function 54 decides whether or not a gain for the first echo data, i.e., data that is a target of adjustment by the adjusting function 51, is a target of gain reduction processing based on the first echo data and color Doppler data. This will be particularly described. The deciding function 54 makes the decision by comparing data values of the first echo data with a first threshold th1, and moreover, comparing data values of the color Doppler data with a second threshold th2. The first threshold th1 is an exemplary embodiment of the first threshold regarding intensity of echo signals in the present invention. The second threshold th2 is an exemplary embodiment of the second threshold regarding information on motion in the present invention.

Figure 3:
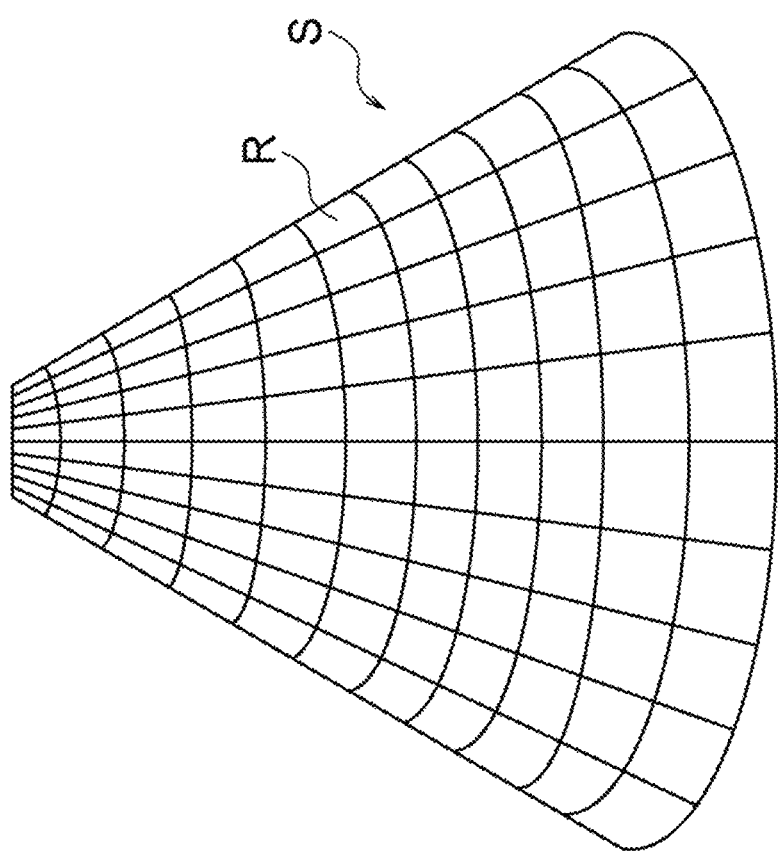
FIG. 3 An explanatory diagram showing each of a plurality of two-dimensional regions that is a target of decision by a deciding function.

The deciding function 54 makes a decision for each of a plurality of two-dimensional regions R into which an area S for an ultrasonic scan (an area of a B-mode image) is divided, as shown in FIG. 3.

The data value of the first echo data is larger for higher signal intensity of an echo signal corresponding to brightness in a B-mode image. The deciding function 54 compares an average AV1 of the data values of the first echo data in each of the plurality of two-dimensional regions R with the first threshold th1. The data value of the color Doppler data is a velocity value in the present embodiment. The deciding function 54 compares an average AV2 of the velocity values in each of the plurality of two-dimensional regions R with the second threshold th2.

The first threshold th1 and second threshold th2 are stored in the storage circuit according to the body part of the subject to/from which ultrasound transmission/reception is performed. In the present embodiment, as the first threshold th1 and second threshold th2, a first threshold th1 and a second threshold th2 that are values according to the body part of the subject including a blood vessel are stored in the storage circuit 8. The first threshold th1 is a value set to intensity of echo signals from ultrasound at a blood vessel wall, for example. The second threshold th2 is a value set to a lowest value expected for motion of blood flow, for example.

Figure 4:
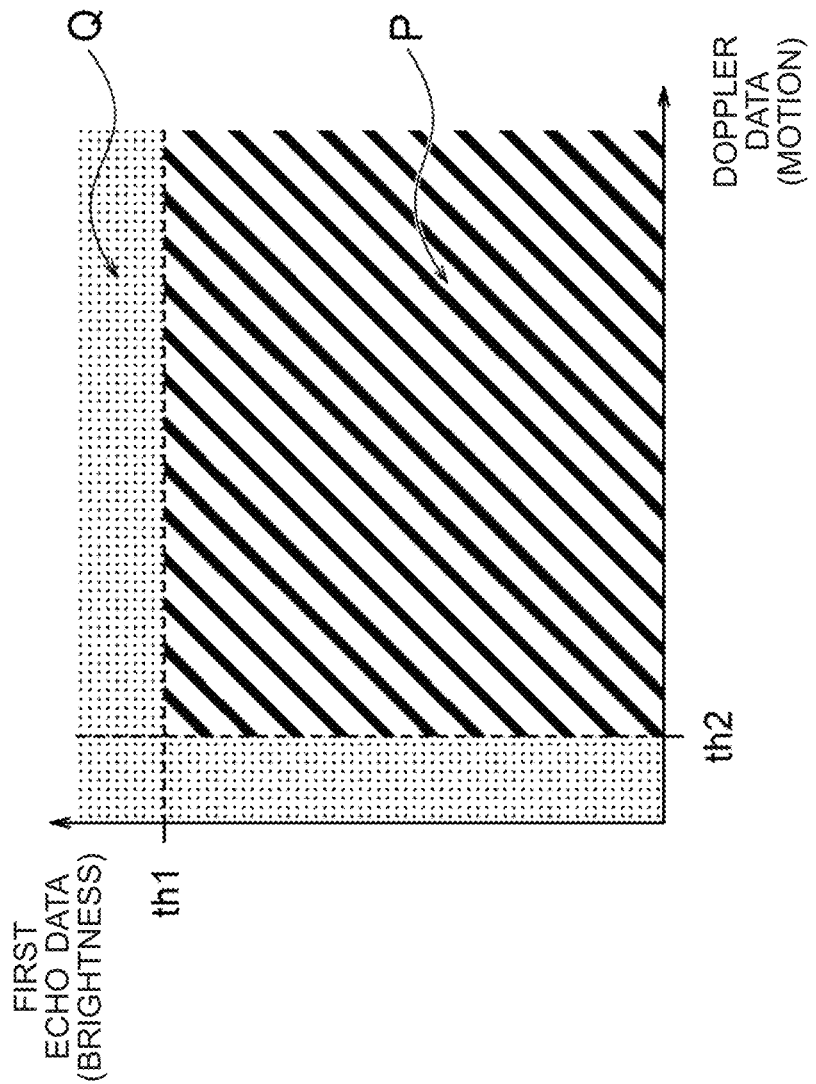
FIG. 4 A diagram for explaining the decision by the deciding function in the present embodiment.

In the case that the average AV1 is smaller than the first threshold th1 and the average AV2 is equal to or greater than the second threshold th2, the deciding function 54 decides that a gain for the first echo data is a target of gain reduction processing. On the other hand, in the case that the average AV1 is equal to or greater than the first threshold th1 or the average AV2 is smaller than the second threshold th2, the deciding function 54 decides that a gain for the first echo data is not a target of gain reduction processing. Referring to FIG. 4, a portion P indicated with hatching is a region in which the average AV1 is smaller than the first threshold th1 and the average AV2 is equal to or greater than the second threshold th2. In FIG. 4, a portion Q indicated with dots is a region in which the average AV1 is equal to or greater than the first threshold th1 or the average AV2 is smaller than the second threshold th2.

Figure 5:
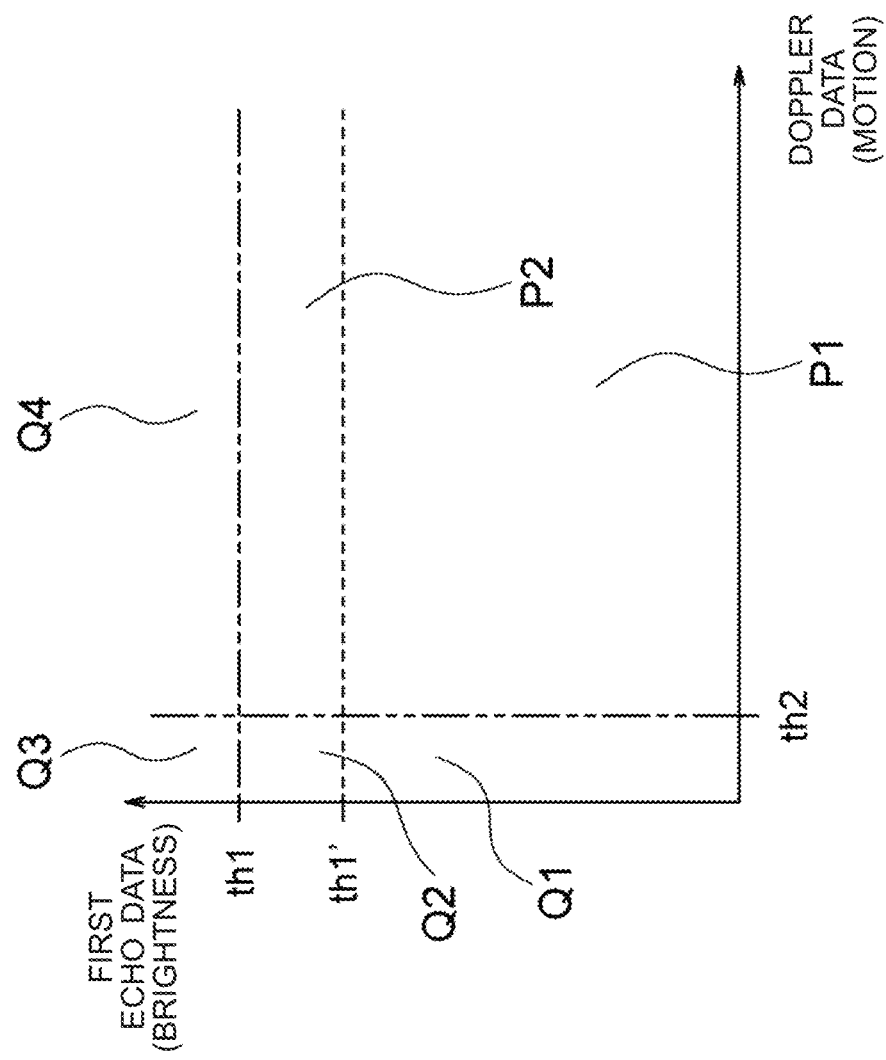
FIG. 5 A diagram for explaining a decision as a comparative example against the decision by the deciding function in the present embodiment.

For example, as a comparative example against the present embodiment will be described a case in which, as shown in FIG. 5, unlike the present embodiment, a first threshold th1' (th1'<th1) is set only for the data values of the first echo data, and a gain for the first echo data is decided to be a target of gain reduction processing when the average AV1 for the first echo data is smaller than the first threshold th1'. In this case, for a portion P1 and a portion Q1 in FIG. 5, a gain for the first echo data is decided to be a target of gain reduction processing. The portion P1 is a region in which the average AV1 for the first echo data is smaller than the first threshold th1' and the average AV2 for the Doppler data is equal to or greater than the second threshold th2. The portion Q1 is a region in which the average AV1 is smaller than the first threshold th1' and the average AV2 for the Doppler data is smaller than the second threshold th2.

On the other hand, for portions P2, Q2, Q3, and Q4 in FIG. 5, a gain for the first echo data is decided not to be a target of gain reduction processing. The portion P2 is a region in which the average AV1 for the first echo data is equal to or greater than the first threshold th1' and is smaller than the first threshold th1, and the average AV2 for the Doppler data is equal to or greater than the second threshold th2. The portion Q2 is a region in which the average AV1 for the first echo data is equal to or greater than the first threshold th1' and is smaller than the first threshold th1, and the average AV2 for the Doppler data is smaller than the second threshold th2. The portion Q3 is a region in which the average AV1 for the first echo data is greater than the first threshold th1 and the average AV2 for the Doppler data is smaller than the second threshold th2. The portion Q4 is a region in which the average AV1 for the first echo data is greater than the first threshold th1 and the average AV2 for the Doppler data is equal to or greater than the second threshold th2.

A region of combined portions P1 and P2 is the portion P. A region of combined portions Q1 to Q4 is the portion Q.

By applying gain reduction processing following the decision described above according to the first threshold th1' shown in FIG. 5 can be reduced noise belonging to the portion P1 occurring within a blood vessel that should be displayed with low brightness in a B-mode image. On the other hand, when multiple reflection of ultrasound caused by a blood vessel wall occurs within a blood vessel, the data value of the first echo data sometimes reaches the first threshold th1' or higher (the portion P2). In this case, gain reduction processing is not applied and noise cannot be reduced. On the contrary, when the data value of the first echo data belongs to the portion Q1, gain reduction processing is applied. The portion Q1, however, is a portion in which much motion is not found in the subject and brightness is not very high in a B-mode image, which probably corresponds to tissue of the subject. The gain reduction processing applied to a gain for echo data obtained from tissue unfavorably causes the tissue portion to be displayed with low brightness in a B-mode image.

By making the decision described above with the first threshold th1' set to a higher value, for example, up to a value equal to the first threshold th1, the aforementioned multiple reflection-induced noise in a blood vessel can be reduced. A higher first threshold th1', however, causes a gain for the echo data from tissue to be regarded as a target of gain reduction processing.

Accordingly, in the present embodiment, the deciding function 54 makes a decision using the data values of the first echo data, and in addition, the data values of the color Doppler data that include information on motion, whereby a gain for the first echo data obtained from the regions R corresponding to the portion P1, and in addition, to the portion P2 can be regarded as a target of gain reduction processing. Thus, the multiple reflection-induced noise in a blood vessel can be reduced. On the other hand, a gain for the first echo data obtained from the regions R corresponding to the portions Q2 to Q4, and in addition, to the portion Q1 can be excluded from a target of gain reduction processing. This achieves a more precise decision as to whether or not to perform gain reduction processing.

The gain setting function 55 sets a gain for the first echo data for each of the plurality of regions R. The gain setting function 55 sets the gain decided by the deciding function 54 to be a target of gain reduction processing to a gain less than one. On the other hand, the gain setting function 55 sets the gain decided by the deciding function 54 not to be a target of gain reduction processing to a gain equal to one or more. In the case that a gain equal to one or more is set, a gain, to which at least one of TGC (Time Gain Control) processing and LGC (Lateral Gain Control) processing discussed later is applicable, may be set depending upon the position of a region R.

The adjusting function 51 performs adjustment on the first echo data using the gain set by the gain setting function 55. When the gain is less than one, the adjusting function 51 applies attenuation processing to the first echo data. This can reduce noise. On the other hand, when the gain is greater than one, the adjusting function 51 applies enhancement processing to the first echo data. It should be noted that when the gain is equal to one, the adjusting function 51 outputs data values of the first echo data to the B-mode processing function 52 without any change.

When the gain is equal to one or more, at least one of TGC processing and LGC processing is performed by the adjusting function 51. The echo data obtained by the adjusting function 51 is subjected to B-mode processing by the B-mode processing function 52, and B-mode data is created. The image data creating function 56 then creates B-mode image data based on the B-mode data, and a B-mode image is displayed on the display device.

Figure 6:
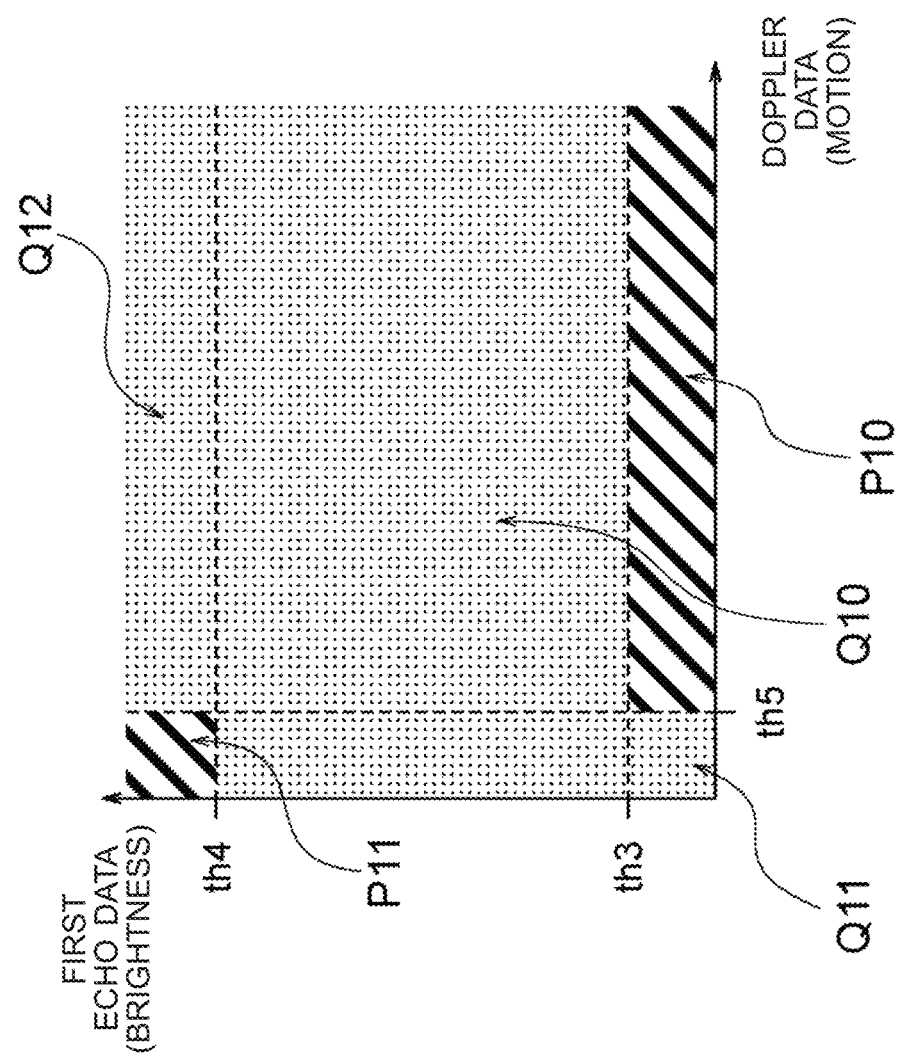
FIG. 6 A diagram for explaining the decision by the deciding function in a variation of the present embodiment.

Next, a variation will be described. An example in which a B-mode image is acquired for a body part in a subject to be examined including a heart will be described. In this variation, as thresholds related to the first echo data, a third threshold th3 and a fourth threshold th4 (th3<th4) shown in FIG. 6 are stored in the storage circuit 8. Moreover, as a threshold related to the color Doppler data, a fifth threshold th5 is stored. It should be noted that the scale in FIG. 6 is different from those in FIGS. 4 and 5.

The third threshold th3 is a value set to lowest signal intensity expected as intensity of echo signals from ultrasound in cardiac tissue. The fourth threshold th4 is a value set to signal intensity of echo signals from a bone, such as a rib, for example. The third threshold th3 and fourth threshold th4 constitute exemplary embodiments of the first threshold regarding the intensity of echo signals, and the third and fourth thresholds in the present invention. The fifth threshold th5 is a value set to a lowest value expected for motion in the heart, for example. The fifth threshold th5 is an exemplary embodiment of the second threshold regarding information on motion in the present invention.

The deciding function 54 makes the decision described earlier by comparing an average AV1 of data values of the first echo data with the third threshold th3 and fourth threshold th4, and moreover, comparing an average AV2 of velocity values of the color Doppler data with the fifth threshold th5. More specifically, when the average AV1 is smaller than the third threshold th3 and the average AV2 is equal to or greater than the fifth threshold th5, the deciding function 54 decides that a gain for the first echo data is a target of gain reduction processing. In FIG. 6, a portion P10 indicated with hatching is a region in which the average AV1 is smaller than the third threshold th3 and the average AV2 is equal to or greater than the fifth threshold th5.

Moreover, when the average AV1 is equal to or greater than the fourth threshold th4 and the average AV2 is smaller than the fifth threshold th5, the deciding function 54 also decides that a gain for the first echo data is a target of gain reduction processing. In FIG. 6, a portion P11 indicated with hatching is a region in which the average AV1 is equal to or greater than the fourth threshold th4 and the average AV2 is smaller than the fifth threshold th5.

On the other hand, the deciding function 54 decides that a gain for the first echo data is not a target of gain reduction processing when the average AV1 is equal to or greater than the third threshold th3 and is smaller than the fourth threshold th4, when the average AV1 is smaller than the third threshold th3 and the average AV2 is smaller than the fifth threshold th5, and when the average AV1 is equal to or greater than the fourth threshold th4 and the average AV2 is equal to or greater than the fifth threshold th5. In FIG. 6, a portion Q10 indicated with dots is a region in which the average AV1 is equal to or greater than the third threshold th3 and is smaller than the fourth threshold th4. Moreover, in FIG. 6, a portion Q11 similarly indicated with dots is a region in which the average AV1 is smaller than the third threshold th3 and the average AV2 is smaller than the fifth threshold th5. Furthermore, in FIG. 6, a portion Q12 similarly indicated with dots is a region in which the average AV1 is equal to or greater than the fourth threshold th4 and the average AV2 is equal to or greater than the fifth threshold th5.

For example, as a comparative example against the present embodiment will be described a case in which, unlike the present embodiment, no thresholding decision is made for the average AV2 for the Doppler data, and only the third threshold th3 is set for data values of the first echo data, and therefore a gain for the first echo data is decided to be a target of gain reduction processing when the average AV1 for the first echo data is smaller than the third threshold th3. In this case, for the portion P11 in FIG. 6, a gain for the first echo data is decided not to be a target of gain reduction processing. The portion P11, however, is a portion in which much motion is not found in the subject and brightness is relatively high in a B-mode image. In the case that a portion has relatively high brightness in a B-mode image of a body part including a heart and no motion is found in that portion, it is probably noise appearing due to bone reflection. However, since the average AV1 for the first echo data is not smaller than the third threshold th3, gain reduction processing is not applied, and in turn, noise cannot be reduced.

Moreover, in the case that a gain for the first echo data is decided to be a target of gain reduction processing for an average AV1 for the first echo data smaller than the third threshold th3, the portion Q11 in FIG. 6 is regarded as a target of gain reduction processing. Here sometimes encountered is a case in which immediately after acquiring an ultrasonic image for a body part including a heart, an ultrasonic image for a liver is also acquired with the same imaging conditions as those for the body part including the heart. In this case, in spite of the fact that hepatic tissue may be included in the portion Q11 in FIG. 6, gain reduction processing is applied, which unfavorably causes the portion to be displayed with low brightness in a B-mode image.

Accordingly, in the present embodiment, the portion P11 may be regarded as a target of gain reduction processing by the deciding function 54 making a decision using data values of the first echo data, and in addition, data values of the color Doppler data including information on motion. Thus, noise affected by bone reflection can be reduced. Moreover, in the present embodiment, the portion Q11 can be excluded from a target of gain reduction processing, and therefore, hepatic tissue, for example, can be better imaged in a B-mode image.

While the present invention has been described with reference to the embodiments above, it will be easily recognized that the present invention may be practiced with several modifications without departing from the spirit and scope thereof. For example, in place of the velocity value, a power value may be used as the data value of color Doppler data. Moreover, in place of the color Doppler processing, power Doppler processing, pulsed Doppler processing, or continuous-wave Doppler processing may be performed as the Doppler processing by the Doppler processing function 53 to detect information on motion in a subject.

Figure 7:
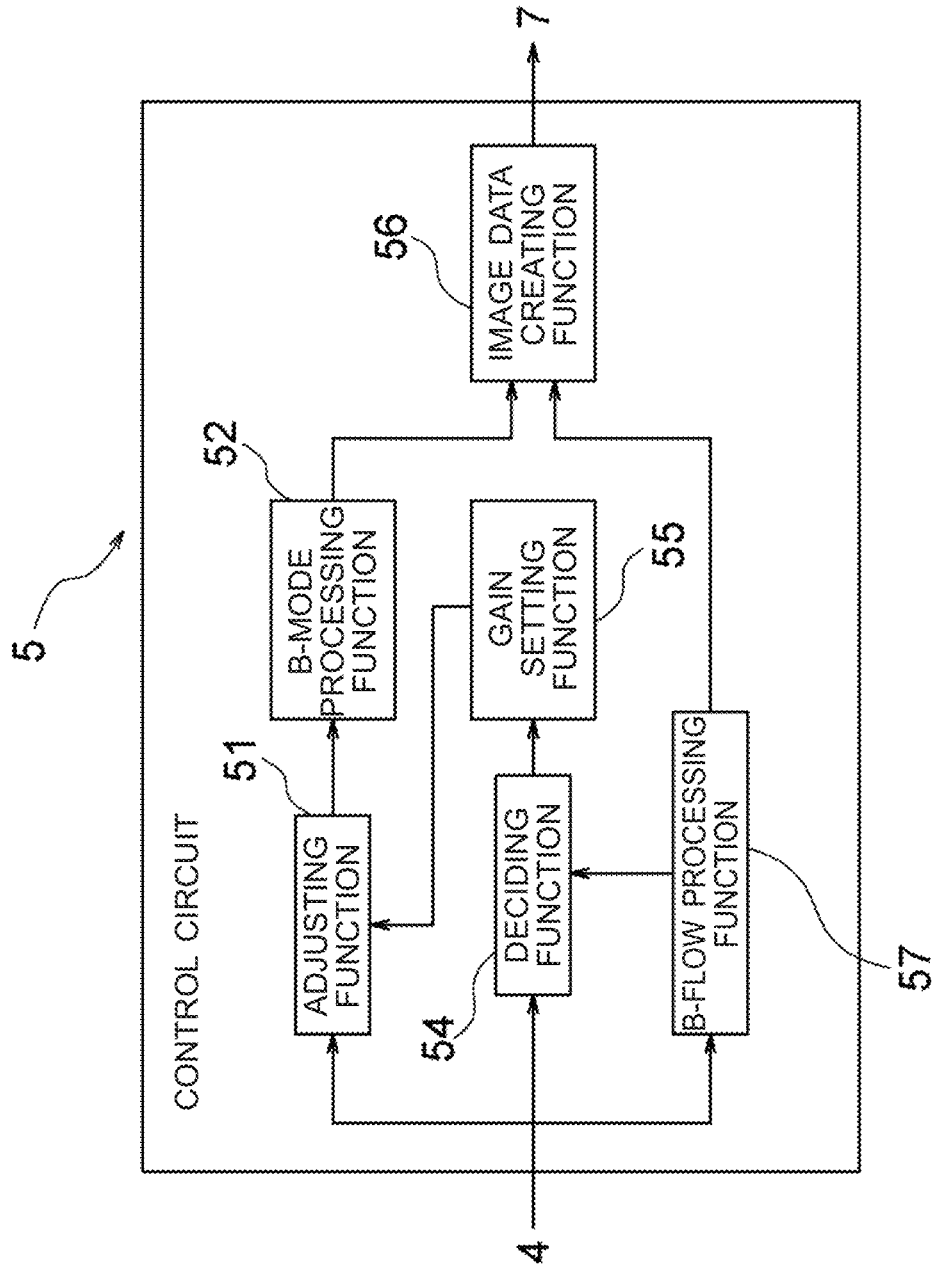
FIG. 7 Another exemplary block diagram of functions of the control circuit in the ultrasonic diagnostic apparatus in the embodiment.

Furthermore, as shown in FIG. 7, the control circuit 5 may be configured to execute a B-flow processing function 57 in place of the Doppler processing function 53. In this case, the deciding function 54 makes the decision described earlier using information on motion, such as a velocity value in a subject contained in B-flow data obtained by the B-flow processing function 57, in place of the Doppler data.

In addition, as the information on motion in a subject, two kinds of information (a velocity value and a power value, for example) may be used. In this case, the deciding function 54 may make a decision as to whether or not a gain is a target of gain reduction processing using three axes including data values of the first echo data, and the two kinds of motion information.

Figure 8:
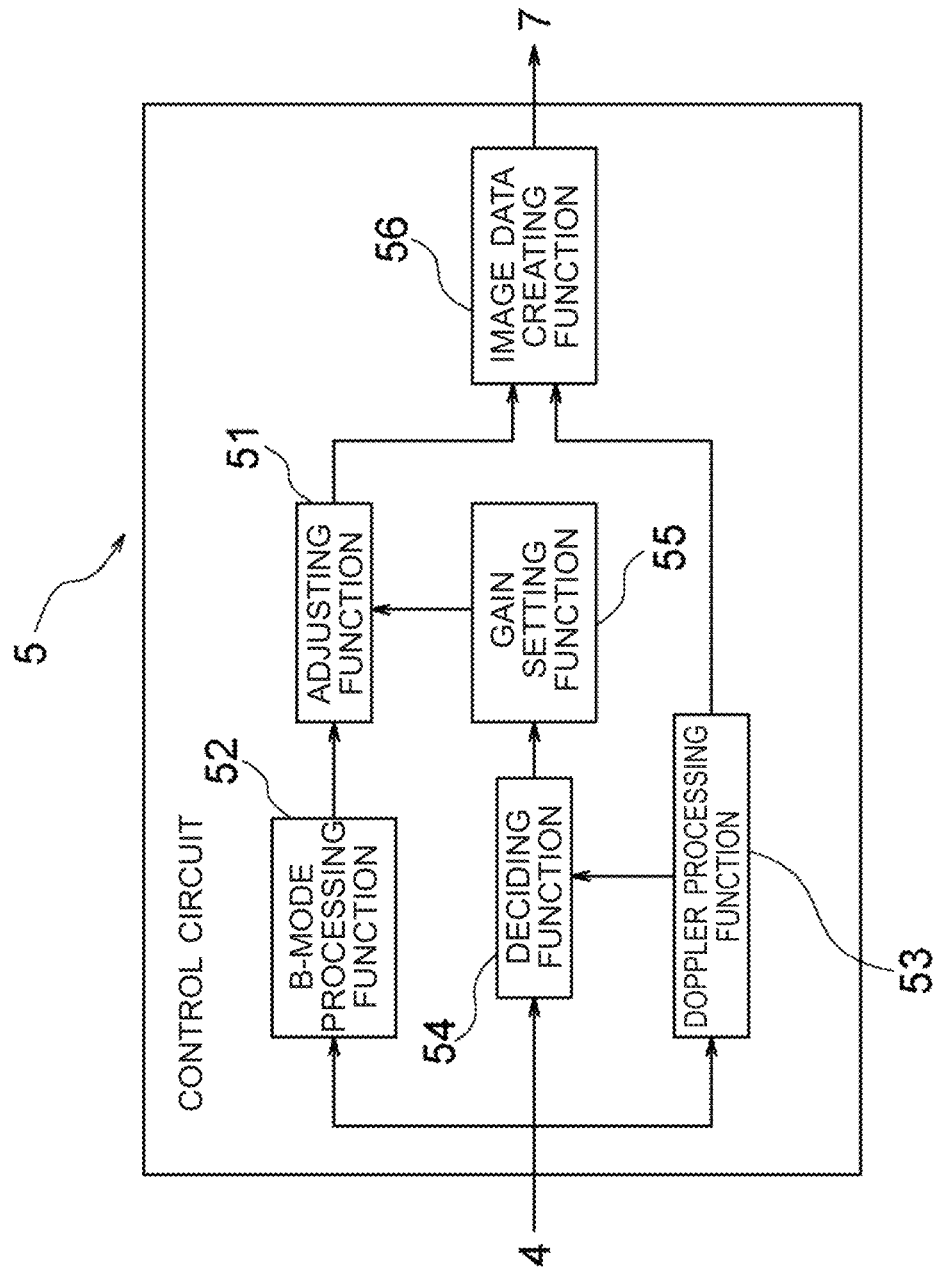
FIG. 8 Still another exemplary block diagram of functions of the control circuit in the ultrasonic diagnostic apparatus in the embodiment.

Moreover, as shown in FIG. 8, the B-mode processing function 52 and adjusting function 51 may change places in the control circuit 5. Specifically, B-mode processing may be applied to the echo data output from the reception circuit 4 by the B-mode processing function 52 to create B-mode data, and adjustment by the adjusting function 51 may be applied to the B-mode data.

Furthermore, B-mode-imaging ultrasound, and ultrasound for performing Doppler processing or B-flow processing may be common. For example, Doppler processing or B-flow processing may be performed based on echo signals from B-mode-imaging ultrasound. Alternatively, a B-mode image may be produced based on echo signals from Doppler-processing or B-flow-processing ultrasound.

In addition, the embodiment described above may be a method of controlling an ultrasonic apparatus, the method comprising:

creating, based on echo signals from first ultrasound transmitted to a subject to be examined, data for an ultrasonic image having display information depending upon intensity of said echo signals;

detecting information on motion in said subject based on echo signals from second ultrasound transmitted to said subject; and deciding whether or not a gain for the echo signals from said first ultrasound is a target of gain reduction processing based on the intensity of the echo signals from said first ultrasound and on said information on motion.

DESCRIPTION OF REFERENCE SYMBOLS

1 Ultrasonic diagnostic apparatus
5 Control circuit
8 Storage circuit
51 Adjusting function
52 B-mode processing function
53 Doppler processing function
54 Deciding function
55 Gain setting function
56 Image data creating function
57 B-flow processing function

The invention claimed is:
1. An ultrasonic apparatus comprising:
an ultrasonic probe including ultrasonic transducers;
an input device;
a display device;
a transmission circuit;
a reception circuit; and
a control circuit, wherein the control circuit is configured to:
control the ultrasonic probe to acquire first echo data from a target area using B-mode-imaging ultrasound transmission;
control the ultrasonic probe to acquire second echo data from the target area using Doppler-processing ultrasound transmission;
apply Doppler processing to the second echo data to obtain Doppler data;
divide the target area into a plurality of regions;
identify one or more of the plurality of regions for gain reduction based on, for each of the plurality of regions, both a comparison of the first echo data to a first threshold and a comparison of the Doppler data to a second threshold, wherein the identified one or more of the plurality of regions each has an average first echo data value smaller than the first threshold and an average color Doppler data value equal to or greater than the second threshold;
set a gain for each of the plurality of regions, wherein setting the gain comprises applying attenuation pro- cessing to the first echo data from each of the identified one or more of the plurality of regions;

apply B-mode processing to the first echo data, after the gain has been set for each of the plurality of regions, to create B-mode image data;

display the B-mode image on the display device.

2. The ultrasonic apparatus of claim 1, further comprising a storage circuit, wherein the first threshold and the second threshold are stored in the storage circuit according to a body part of the subject.

3. The ultrasonic apparatus of claim 2, wherein the body part includes at least one of a blood vessel and a heart.

4. The ultrasonic apparatus of claim 1, wherein the first threshold is a value set to intensity signals from ultrasound at a blood vessel wall, and the second threshold is a value set to a lowest value expected for motion of blood flow.

5. The ultrasonic apparatus of claim 1, wherein the Doppler processing is at least one of color Doppler processing, power Doppler processing, pulsed Doppler processing, and continuous-wave Doppler processing.

6. The ultrasonic apparatus of claim 1, wherein the control circuit is configured to set the gain using at least one of TGC (Time Gain Control) processing and LGC (Lateral Gain Control) processing.

7. A method of applying gain reduction in ultrasonic imaging, the method comprising:

controlling an ultrasonic probe to acquire first echo data from a target area using B-mode-imaging ultrasound transmission;

controlling the ultrasonic probe to acquire second echo data from the target area using Doppler-processing ultrasound transmission;

applying Doppler processing to the second echo data to obtain Doppler data;

dividing the target area into a plurality of regions;

identifying one or more of the plurality of regions for gain reduction based on, for each of the plurality of regions, both a comparison of the first echo data to a first threshold and a comparison of the Doppler data to a second threshold, wherein the identified one or more of the plurality of regions each has an average first echo data value smaller than the first threshold and an average color Doppler data value equal to or greater than the second threshold;

setting a gain for each of the plurality of regions, wherein setting the gain comprises applying attenuation processing to the first echo data from each of the identified one or more of the plurality of regions;

applying B-mode processing to the first echo data, after the gain has been set for each of the plurality of regions, to create B-mode image data; and displaying the B-mode image on a display device.

8. The method of claim 7, further comprising storing the first threshold and the second threshold in a storage circuit according to a body part of the subject, wherein the storage circuit includes different values for the first threshold and the second threshold for different body parts.

9. The method of claim 8, wherein the body part includes at least one of a blood vessel and a heart.

10. The method of claim 7, wherein the first threshold is a value set to intensity signals from ultrasound at a blood vessel wall, and the second threshold is a value set to a lowest value expected for motion of blood flow.

11. The method of claim 7, wherein the Doppler processing is at least one of color Doppler processing, power Doppler processing, pulsed Doppler processing, and continuous-wave Doppler processing.

12. The method of claim 7, wherein setting the gain comprises using at least one of TGC (Time Gain Control) processing and LGC (Lateral Gain Control) processing.

* * * * *